US008177896B2

(12) United States Patent
Qian et al.

(10) Patent No.: US 8,177,896 B2
(45) Date of Patent: May 15, 2012

(54) ANTIFOULING FURAN-2-ONE DERIVATIVES

(75) Inventors: Peiyuan Qian, Hong Kong (CN); Ying Xu, Hong Kong (CN); Xiaojian Zhou, Yangzhou (CN); Hongping He, Hong Kong (CN); Nobuhiro Fusetani, Hakodate (JP); Wei-Min Dai, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 0 days.

(21) Appl. No.: 13/054,938

(22) PCT Filed: Apr. 16, 2009

(86) PCT No.: PCT/CN2009/071302
§ 371 (c)(1),
(2), (4) Date: Feb. 21, 2011

(87) PCT Pub. No.: WO2010/009632
PCT Pub. Date: Jan. 28, 2010

(65) Prior Publication Data
US 2011/0185944 A1     Aug. 4, 2011

Related U.S. Application Data

(60) Provisional application No. 61/129,863, filed on Jul. 24, 2008, provisional application No. 61/193,383, filed on Nov. 21, 2008.

(51) Int. Cl.
C09D 5/16       (2006.01)
C07D 307/33    (2006.01)
A01N 25/00     (2006.01)
A01N 31/08     (2006.01)

(52) U.S. Cl. .............. 106/15.05; 514/461; 523/177; 549/263; 549/295; 549/305

(58) Field of Classification Search .............. 106/15.05; 514/461; 523/177; 549/263, 295, 305
See application file for complete search history.

(56) References Cited

U.S. PATENT DOCUMENTS 5,248,221 A * 9/1993 Gerhart et al. .............. 405/216

OTHER PUBLICATIONS

De-Hai Li et al, "Four Butenolides are Novel Cytotoxic Compounds Isolated from the Marine-Derived Bacterium, Streptoverticillium luteoverticillatum 11014", Arch Pharm Res. vol. 29, No. 8, pp. 624-626, 2006 (no month).*

Chemical Abstract Accession No. 2008:2007002, Document No. 148:533331, Ray et al, "Chemical composition and antimicrobial activity of the leaf oil from Sysygium gardneri", Journal or Essential Oil Research (2007) vol. Date 2008, 20(1), 72-74 (no month).*
Chemical Abstract Registry No. 2305-05-07, Compound: 2(3H)-Furanone, dihydro-5-octyl-, Entered STN Nov. 16, 1984.*
Yu Zhang, et al, "Comparative Proteome and Phosphoproteome Analyses during Cyprid Development of the Barnacle Balanus amphitrite", Journal of Proteome Research 2010, 9, 3146-3157.
Pei-Yuan Qian, et al. "Changes in the proteome and phosphoproteome expression in the bryozoan Bugula neritina larvae in response to the antifouling agent butenolide", Proteomica 2010, 10, 3435-3446.
Yi-Fan Zhang, et al, "The effect of butenolide on behavioral and morphological changes in two marine fouling species, the barnacle Balanus amphitrite and the bryozoan Bugula neritina".
Yi-Fan Zhang, et al, "Acute toxicity of the antifouling compound butenolide in non-target organisms".
Ying Xu, et al. "Potent antifouling compounds produced by marine Streptomyces", Bioresource Technology 101 (2010) 1331-1336.
Wei-Min Dai, et al. "Total synthesis of (4S,10R)-4-hydroxy-10-methyl-11-oxododec-2-en-1,4-olide and related bioactive marine butenolides", Tetrahedron: Asymmetry 19 (2008) 1549-1556.
Yan Wang, et al. "Total synthesis of diastereomeric marine butenolides possessing a syn-aldol subunit at C10 and C11 and the related C11-ketone", Tetrahedron 66 (2010) 187-196.
De-Hai Li et al, "Four butenolides are novel cytotoxic compounds isolated from the marine-derived bacterium, Strreptoverticillium luteoverticillatum 11014", Arch Pharm Res vol. 29, No. 8, 624-626, 2006.
Angelo Pecunioso, et al, "Nitrodienic-like reactivity of 2-nitrofuran with organometallic reagents: one-step synthesis of alkylfuranones", Tetrahedron vol. 46, No. 21, pp. 7497-7508, 1990.
International Preliminary Report on Patentability of PCT application No. PCT/CN2009/071302 filed on Apr. 16, 2009.

* cited by examiner

*Primary Examiner* — Anthony J Green
(74) *Attorney, Agent, or Firm* — George G. Wang; Wilkinson & Grist

(57) ABSTRACT

A novel chemical genus of furan-2-one antifouling compound as non-toxic, environment friendly antifouling agent, a coating material for objects submerged under the water based on the furan-2-one compounds. The substituted furan-2-one antifouling compounds have a furan-2-one ring and an alkyl side chain thereto and are of the formula:

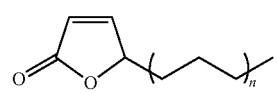

I where n=6-14, representing the number of carbon atoms in said side chain.

14 Claims, 16 Drawing Sheets

ANTIFOULING FURAN-2-ONE DERIVATIVES

CROSS REFERENCE

This application claims benefit from U.S. Provisional Patent Application Nos. 61/129,863 and 61/193,383, filed Jul. 24, 2008 and Nov. 21, 2008, respectively. The contents of the prior applications are incorporated herein by reference.

FIELD OF THE INVENTION

The present invention relates to antifouling methods and materials based on nontoxic bioactive agents. Particularly, it relates to novel nontoxic antifouling compounds which belong to a substituted furan-2-one genus.

BACKGROUND OF THE INVENTION

Biofouling is the undesirable accumulation of micro-organisms, plants, and animals on artificial surfaces immersed in water such as ship hulls, docks, buoys, etc. More than 4000 organisms having been reported as being species causing biofouling, including bacteria, micro-algae, macro-algae, sea-grass, molluscs, crustacean, etc. Most fouling-causing organisms have a swimming larval stage followed by a sedentary adult stage that remains attached to its substratum throughout the remainder of its life. The attached adult organisms can increase frictional resistance on the hulls of ships, increase the weight of buoys, increase oil flat loading weight, block seawater pipes, decrease water exchange through aquaculture net boxes, and compete for space and food with cultured shellfish, among other negative effects.

The global economic costs due to biofouling are extremely large. For example, biofouling of ships' hulls leads to the high frictional resistance, increase of weight, and subsequent potential speed reduction and loss of maneuverability. As a result, higher fuel consumption is needed, causing increased emissions of harmful compounds. It may also entail a need for heavier and energetically efficient machinery. The estimated economic loss caused by biofouling is around US$ 6 billion annually. The use of a typical antifouling agent (tributyltin) on ship hulls, has saved the US Navy an estimated US$150 million each year. Because of these large-scale economic consequences, development of efficient antifouling methodologies is crucial.

Traditionally, antifouling materials are metal based. Prior to the 17th century, plumbum was the most common antifouling agent. From 1960's until recently, organotins, represented by tributyltin (TBT), were common anti-fouling agents. However, environmental concerns over the effect of organotins first arose in France, where severe problems were encountered in commercial oyster fisheries in areas where there was intense boating activity and poor tidal exchange. Since then, the distribution, fate and effects of organotins and other antifoulants on the marine and freshwater environment have been under intense scrutiny. Research suggests damaging effects of organotins on reproduction and growth of various marine life. In addition, TBT is known to threaten non-target organisms in the marine ecosystem, causing dramatic effects on shell fishes by inducing imposex in large populations. At concentrations as low as 1 ng/L, TBT can induce imposex. Now, TBT is regarded as one of the most toxic and hazardous compounds introduced into marine environments. In response to these concerns, the Marine Environment Protection Committee (MEPC) of the International Maritime Organization (IMO) has implemented a ban on the application of TBT paints from 1 Jan. 2003, with the intent that no TBT paints will remain on vessels after 1 Jan. 2008.

As an alternative, vessels are increasingly painted with copper-based paints. However, copper-based paints also have negative effects on the marine environment. For example, oysters accumulate considerable amounts of copper and copper is toxic to marine algae.

The toxicity concern is not only about TBT, but about all existing antifouling biocides, and has thus stimulated research and development of non-toxic antifouling coatings. The development of a marine paint or paint ingredient that is non-toxic, non-heavy-metal-based, and benign to the marine environment is urgently sought. The present invention provides a novel category of antifouling compounds which are nontoxic and environmental friendly.

SUMMARY OF THE INVENTION

One object of the present invention is to provide a novel category of chemical compounds which are nontoxic but have potent antifouling activities. Another object of the present invention is to provide an antifouling method which is environmental friendly.

This and other objects of the present invention are realized by providing a novel group of butenolides which are substituted furan-2-one compounds. The compounds of this substituted furan-2-one genus have a potent antifouling activity but are non-toxic and environment-friendly. As used in this invention, the term "substituted furan-2-one antifouling compound" means a species of a substituted furan-2-one genus which is substituted by a side chain at position 5 and represented by formula I:

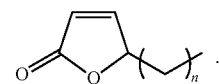

where n=6-14, representing the number of carbon atoms in the side chain and the side chain can be a substituted and branched alkyl group. As particular embodiments, n is between 7-10 and the side chain is non-branched. As a further particular embodiment, n is 8 and the side chain is non-branched and non-substituted, which is 5-octylfuran-2-one:

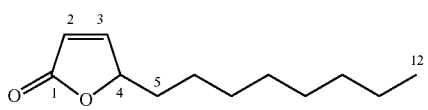

As used in the present application, a "branched" alkyl group means at least one hydrogen on its non-terminal carbon atoms being replaced with a substituent which is connected to the backbone chain with a C—C connection and a "substituted" alkyl group means at least one hydrogen on its backbone carbon atoms being replaced with a substituent without a C—C connection to the backbone chain.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DESCRIPTION OF PARTICULAR EMBODIMENTS OF THE INVENTION

A. The Strains Producing Antifouling Compounds

Figure 1:
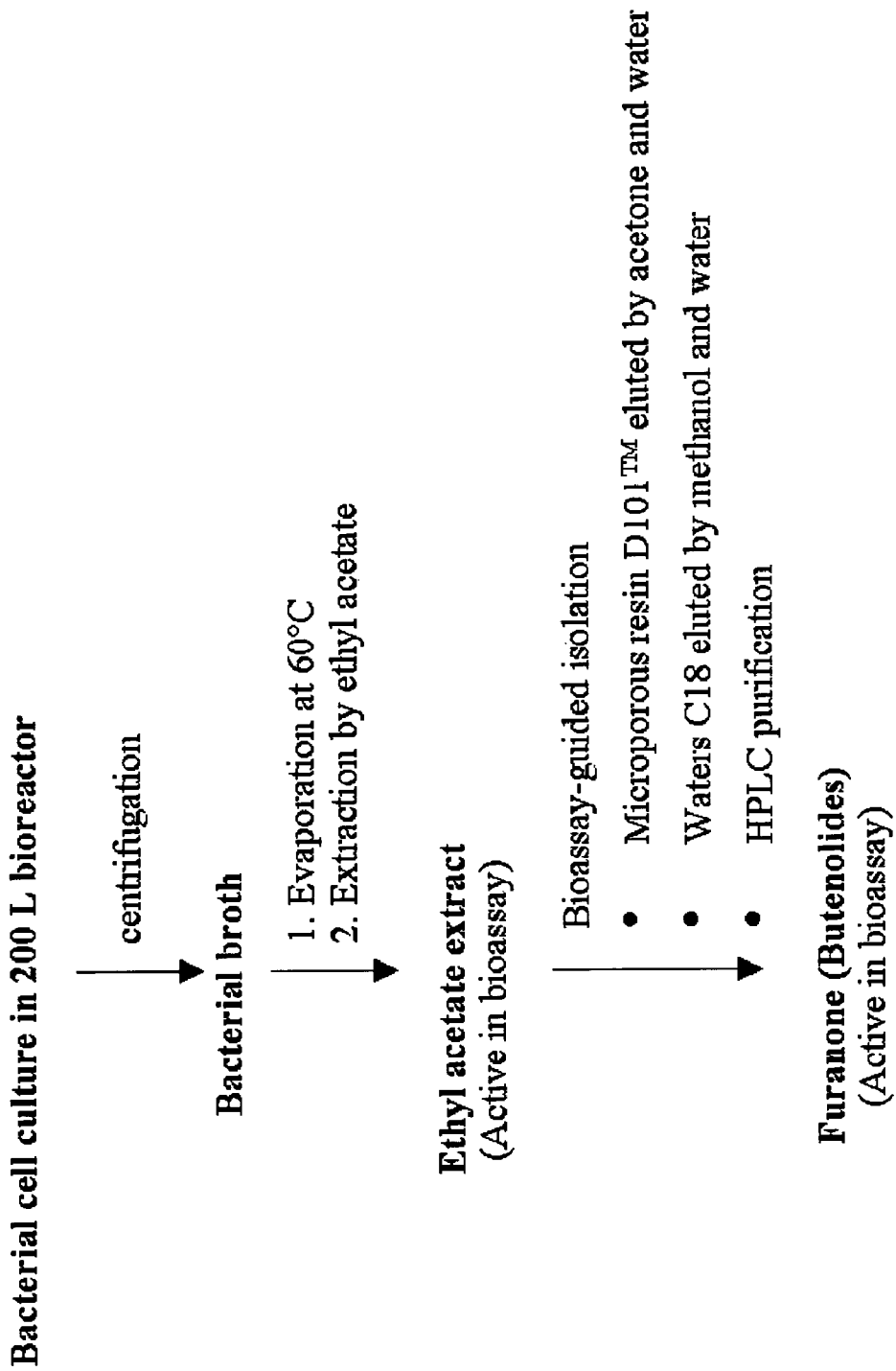
FIG. 1 is the flowchart of a bioassay guided isolation of a substituted furan-2-one antifouling compound from a bacterial strain *Streptomyces albidoflavus* strain UST040711-291.
Figure 2:
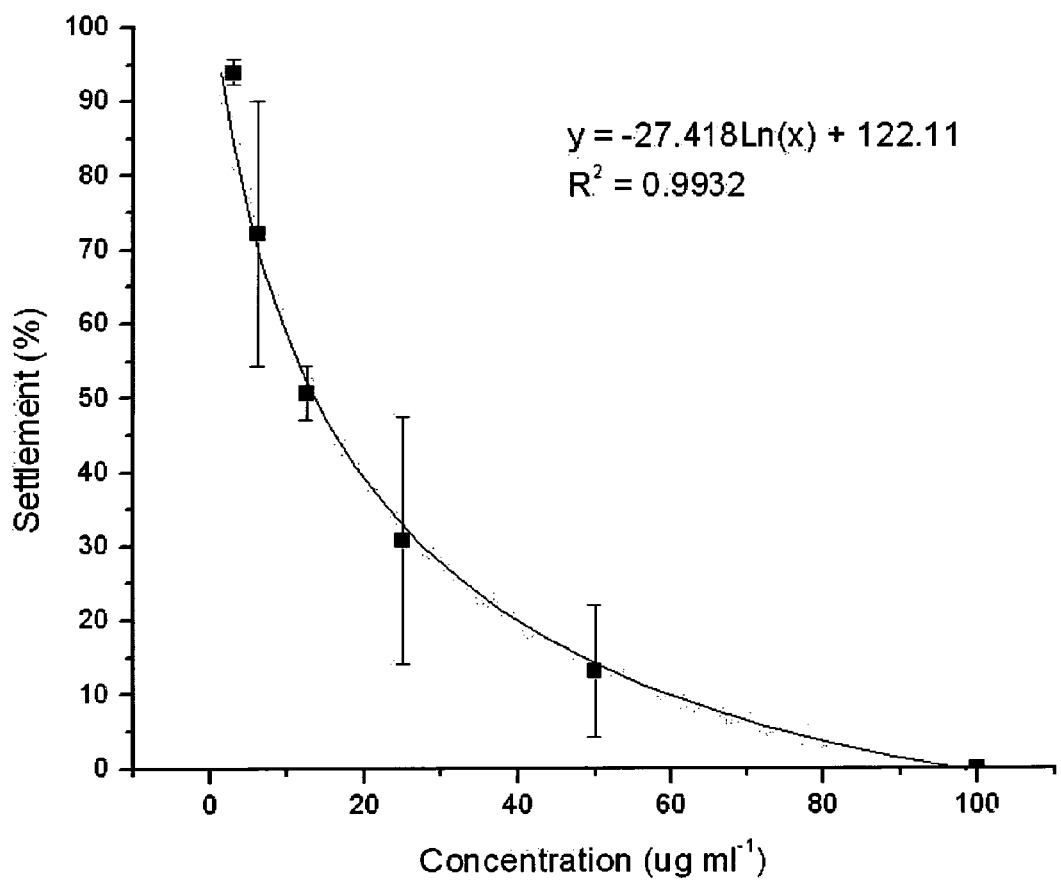
FIG. 2 shows the inhibitory effect of Compound 1 against larval settlement of the barnacle *Balanus aniphitrite*. The results were presented as the mean±standard deviation of at least three replicates (n>=3). The equation analysis was performed by Origin Pro. 7.5.
Figure 3:
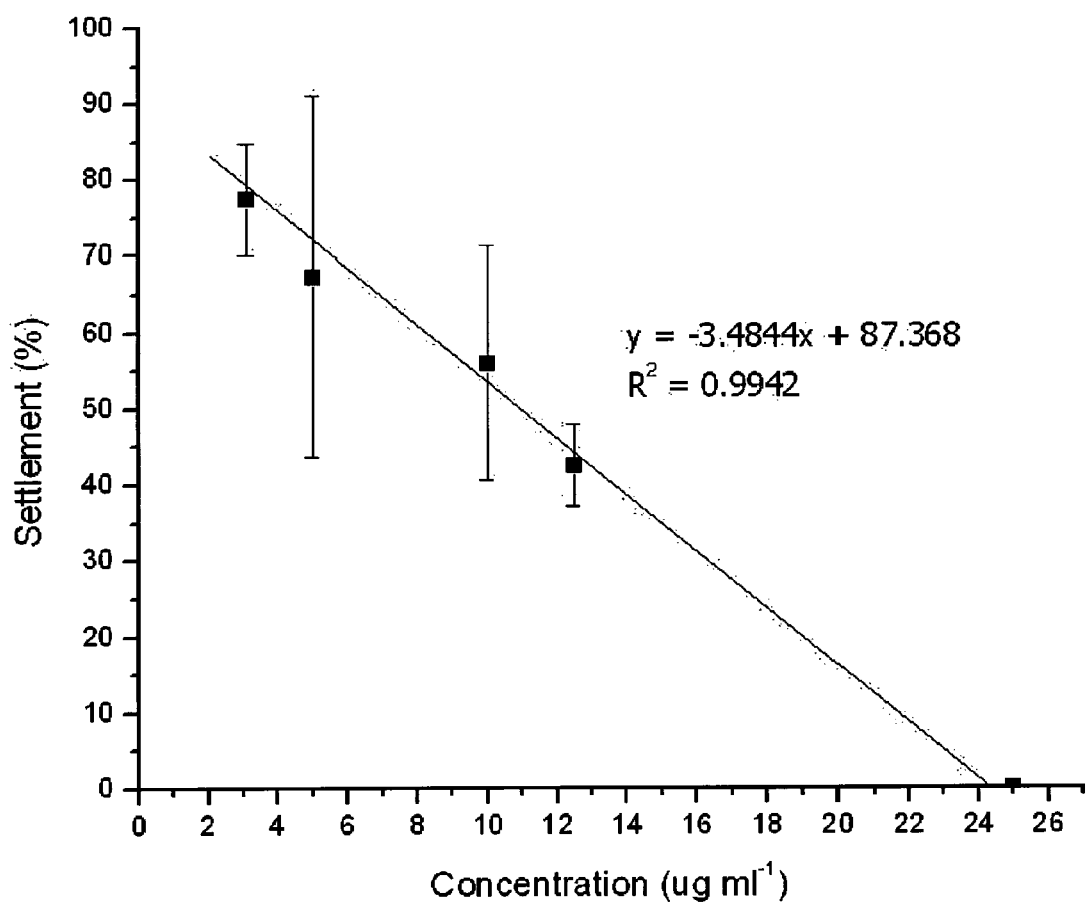
FIG. 3 shows the effect of Compound 1 against larval settlement of the barnacle *Hydroides elegans*. The results were presented as the mean±standard deviation of at least three replicates (n>=3). The equation analysis was performed by Origin Pro. 7.5.
Figure 4:
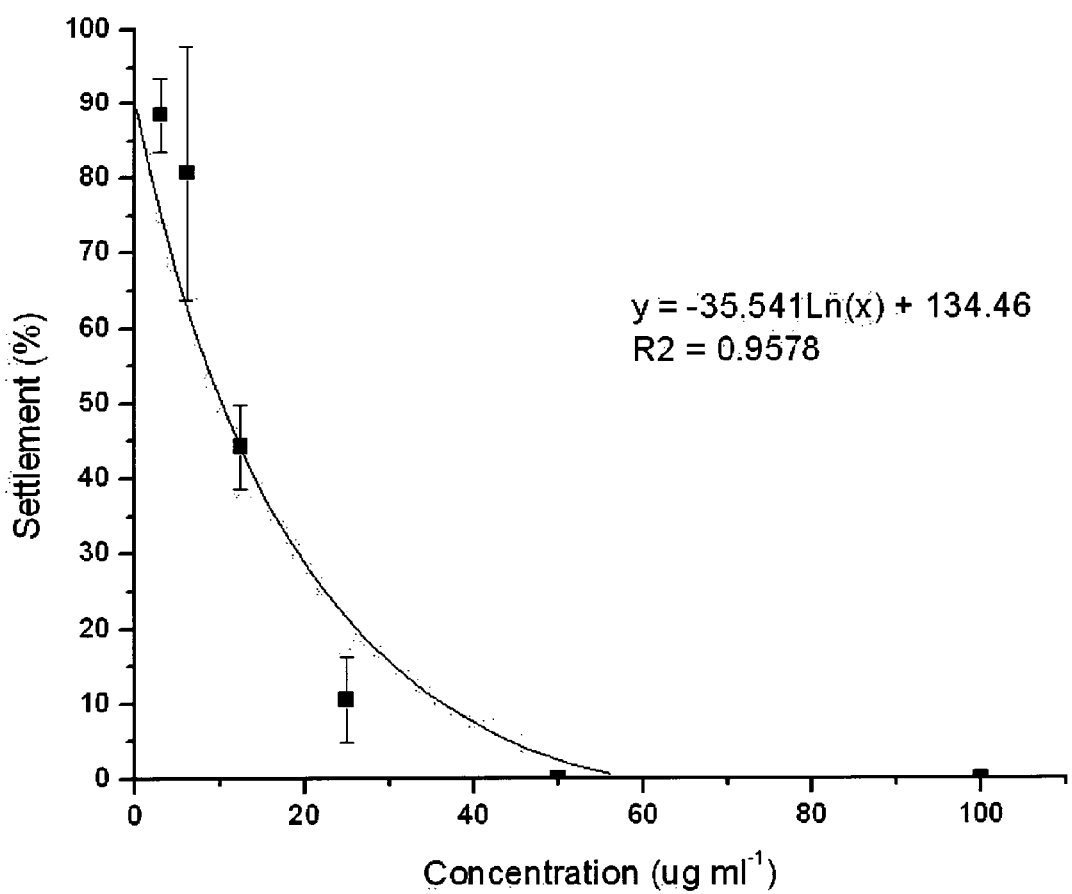
FIG. 4 shows the effect of Compound 2 against larval settlement of the barnacle *Balanus amphitrite*. The results were presented as the mean±standard deviation of at least three replicates (n>=3). The equation analysis was performed by Origin Pro. 7.5.
Figure 5:
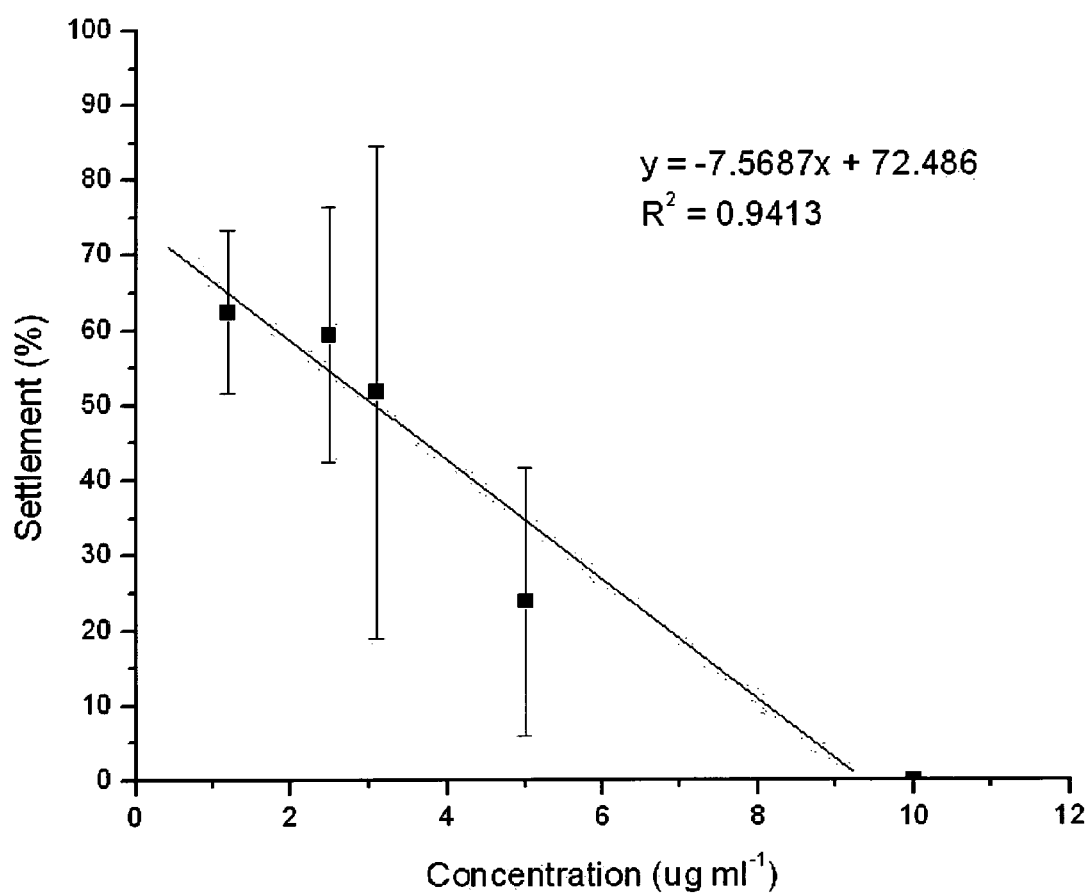
FIG. 5 shows the effect of Compound 2 against larval settlement of the barnacle *Hydroides elegans*. The results were presented as the mean±standard deviation of at least three replicates (n>=3). The equation analysis was performed by Origin Pro. 7.5.

Strain *Streptomyces albidoflavus* strain UST040711-291 was isolated from the sediment sample from 5000 m depth in west Pacific Ocean (N10°50'35"; W154°05'28"). The sediment samples were kept at 0° C. and 4° C. before and after arriving laboratory, respectively.

Strain *S. albidoflavus* strain UST040711-291 was isolated by enrichment techniques as following. Sediment samples of about 1 gram from deep sea were suspended in 10 ml artificial seawater. After mixing, 200 µl of the suspension was spread on 2216E agar plate and incubated in 10° C. Colonies with different shape or color were transferred to new agar plate for new incubation and further isolation. The final identification was conducted by detection of 1.6S rRNA sequence (SEQ ID NO. 3). 16s rRNA sequence was amplified by primer 27F (AGAGTGATCMTGGCTCAG) and 1492R (GGTTACCTTGTTACGACTT) and sequenced, which are referred to as SEQ ID NO. 1 and SEQ ID NO. 2, respectively, in the enclosed Sequence Listing.

The sequence was analyzed for similarity with other known sequences with BLAST program (National Center for Biotechnology Information (NCBI, www.ncbi.nlm.nih.gov/BLAST/). BLAST resulted showed that the strain is *Streptomyces albidoflavus* strain UST040711-291. The sequence has been deposited into the GenBank and the Accession no. is FJ591130.

B. Substituted Furan-2-One Antifouling Compounds Isolated from *Streptomyces albidoflavus* Strain UST040711-291

Fermentation: The bacterium stain *Streptomyces albidoflavus* strain UST040711-291 was cultured in multiple 3 liter flasks containing MGY culture medium (1% of malt extract, 0.4% of glucose, and 0.4% of yeast extract) in seawater at 25° C. with agitation (200 rpm) for 4 days until they reach the stationary phase. In total, 60 liters of bacterial culture were obtained.

Extraction and isolation: The bacterial spent culture broth was firstly separated from the bacterial cells by centrifugation at 5,000 g for 15 min, and then extracted exhaustively by ethyl acetate (EtOAc). The EtOAc phase was then dried under vacuum and the residue was collected. In total, 60 liters of bacterial culture was cumulated and about 12.3 g of crude extract was obtained. The crude extract was subjected to macroporous resin column chromatography using a gradient solvent system from water to acetone, yielding 5 fractions. The acetone-water fraction (3:2) was further purified on an ODS reversed-phase column with a water-methanol solvent system, yielding 10 fractions. Further purification of fraction 4 (40% of methanol) on a HPLC column using an isocratic system of 32% of ACN with a flow of 1 ml min$^{-1}$ yielded compounds 1 to 3. Further purification of fraction 2 (20% of methanol) on a HPLC column using an isocratic system of 30% of ACN with a flow of 1 ml min⁻¹ yielded compound 4 and compound 11.

Optimal production conditions for maximum yield: As shown in Table 2, optimal production conditions for the compound 3, the most active one so far isolated from *Streptomyces albidoflavus* strain UST040711-291 is achieved in a nutrient medium prepared from 1% (w/v) yeast extract and 2% (w/v) glucose in 0.22 μm-filtered seawater with initial pH of 7 and at 24° C. The following table specifies production conditions at different combinations of yeast extract and glucose. The combinations were designed by using statistical model-central component design for 2 factors.

TABLE 2

Design and response of central component design

| Yeast extract (g/L) | Glucose (g/L) | Compound 3 yield (mg/L) |
|---|---|---|
| 8 | 16 | 3.55 |
| 12 | 16 | 5.93 |
| 8 | 24 | 5.73 |
| 12 | 24 | 6.90 |
| 7.2 | 20 | 7.67 |
| 12.8 | 20 | 7.90 |
| 10 | 14.3 | 2.50 |
| 10 | 25.7 | 3.32 |
| 10 | 20 | 9.56 |
| 10 | 20 | 9.27 |
| 10 | 20 | 8.33 |
| 10 | 20 | 9.26 |
| 10 | 20 | 10.04 |

Structure identification: The molecular weight of the compound was determined by negative ESI-MS (Waters Micromass ZQ ESI-MS). The structures of these compounds were identified by means of NMR (¹H NMR, ¹³C NMR, DEPT and COSY). In detail, as following:

Compound 1: ¹H NMR (400 MHz, CDCl₃) δ 7.44 (1H, dd, J=5.9, 1.5 Hz, H3), 6.08 (1H, dd, J=5.9, 2.0 Hz, H-2), 5.02 (1H, dddd, J=7.3, 5.4, 2.0, 1.5 Hz, H-4), 1.75 (1H, m, H-5a), 1.63 (1H, m, H-5b), 1.45 (2H, q, J=7.3 Hz, H-11), 1.41 (2H, m, H-6), 1.38 (2H, m, H-9), 1.33 (2H, m, H-7), 1.31 (2H, m, H-8), 1.10 (3H, s, H-13), 0.86 (3H, t, J=7.3 Hz, H-12); ¹³C NMR (100 MHz, CDCl₃) δ 173.1 (C-1), 156.3 (C-3), 121.4 (C-2), 83.3 (C-4), 72.7 (C-10), 41.0 (C-9), 34.1 (C-11), 33.0 (C-5), 29.8 (C-7), 26.3 (C-13), 24.9 (C-6), 23.5 (C-8), 8.1 (C-12).

Compound 2: ¹H NMR (400 MHz, CDCl₃) δ 7.44 (1H, dd, J=5.7, 1.5, H-3), 6.11 (1H, dd, J=5.7, 1.9, H-2), 5.03 (1H, m, H-4), 3.72 (1H, m, H-11), 1.75 (1H, m, H-5a), 1.70 (1H, m, H-10), 1.62 (1H, m, H-5b), 1.41 (2H, m, H-6), 1.36 (1H, m, H-9a), 1.16 (1H, m, H-9b), 1.32 (2H, m, H-7), 1.28 (2H, m, H-8), 1.14 (3H, d, J=6.4, H-12), 0.88 (3H, d, J=6.8, H-13); ¹³C NMR (100 MHz, CDCl₃) δ 173.2 (C-1), 156.3 (C-3), 121.6 (C-2), 83.4 (C-4), 71.7 (C-12), 40.0 (C-10), 33.2 (C-5), 32.4 (C-9), 29.7 (C-7), 27.1 (C-8), 25.0 (C-6), 20.3 (C-13), 14.6 (C-11).

Compound 3: ¹H NMR (400 MHz, CDCl₃) δ 7.43 (1H, dd, J=5.7, 1.5 Hz, H-3), 6.08 (1H, dd, J=5.7, 2.0 Hz, H-2), 5.01 (1H, dddd, J=7.3, 5.4, 2.0, 1.5 Hz, H-4), 2.47 (1H, tq, J=7.4, 6.8 Hz, H-10), 2.11 (3H, s, H-12), 1.75 (1H, dddd, J=13.7, 9.8, 5.9, 5.4 Hz, H-5a), 1.63 (1H, m, H-9a), 1.31 (H, m, H-9b), 1.60 (1H, m, H-5b), 1.41 (2H, m, H-6), 1.31 (2H, m, H-7), 1.24 (2H, m, H-8), 1.06 (3H, d, J=6.8 Hz, H-13); ¹³C NMR (100 MHz, CDCl₃) δ 212.8 (C-11), 173.1 (C-1), 156.2 (C-3), 121.4 (C-2), 83.2 (C-4), 47.0 (C-10), 32.9 (C-5), 32.5 (C-9), 29.2 (C-7), 26.8 (C-8), 24.7 (C-6), 27.9 (C-12), 16.2 (C-13).

Compound 4: ¹H NMR (400 MHz, CDCl₃) δ 7.44 (1H, dd, J=5.7, 1.5 Hz, H-3), 6.11 (1H, dd, J=5.7, 2.0 Hz, H-2), 5.04 (1H, dddd, J=7.3, 5.9, 2.0, 1.5 Hz, H-4), 1.77 (1H, H-5), 1.67 (1H, m, H-5), 1.48 (2H, m, H-6), 1.45 (2H, m, H-9), 1.36 (4H, m, H-7, H-8), 1.21 (6H, s, H-11, H-12); ¹³C NMR (100 MHz, CDCl₃) δ 173.1 (C-1), 156.2 (C-3), 121.6 (C-2), 83.3 (C-4), 70.9 (C-10), 43.7 (C-9), 33.1 (C-5), 29.8 (C-7), 25.0 (C-6), 29.3 (C-11), 29.2 (C-12), 24.1 (C-8).

Based on above data, these four compounds were identified as:

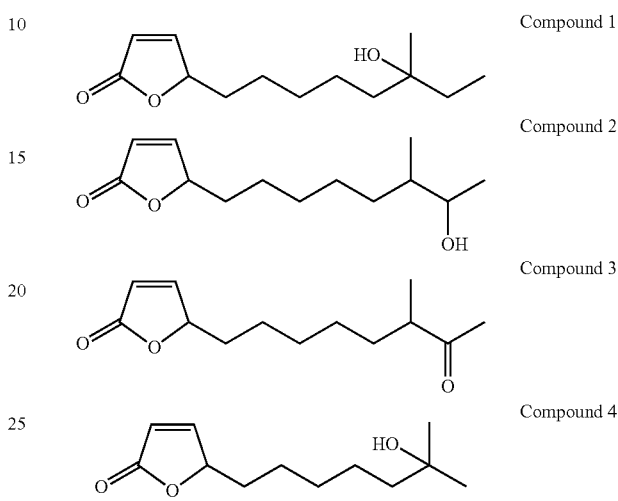

C. Substituted Furan-2-One Antifouling Compounds Chemically Synthesized

As part of structure-function relationship analysis, two substituted furan-2-one antifouling compound were also designed and chemically synthesized, which are referenced to as compound 5 and compound 6.

Chemical synthesis of compound 5: As shown in the following synthetic routine, compound 2 was mixed with compound d in the presence of SiO2 and CH2Cl2 for 1 hour at 30oC, the yield of this reaction is over 90%. Compound 5 was then obtained and purified by HPLC.

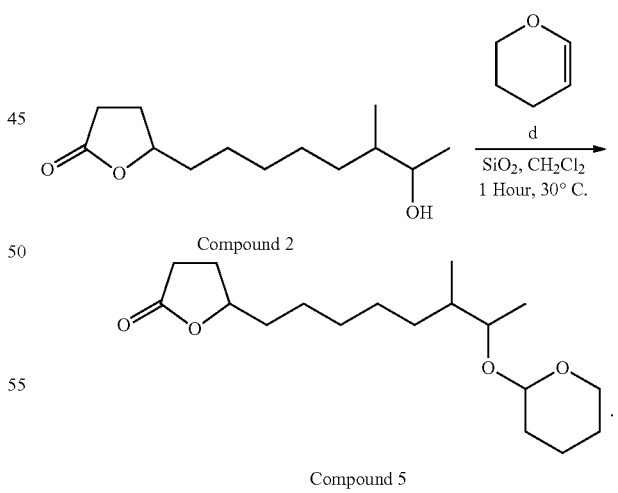

Chemical synthesis of compound 6: As shown in the following routine, methylmagnesium bromide (3.0M, 33 ml, 0.1 mol) in THF was added at 0° C. via syringe to a stirred solution of the propiolic acid (3.5 g, 0.05 mol) in dry THF (100 mL), kept under nitrogen. After the mixture was stirred for 2 h at 0° C., compound a (7.1 g, 0.05 mol) was added via syringe in one portion at 0° C., and the mixture was stirred at 0° C. for 1 h and allowed to warm to room temperature for 1 h. The mixture was acidified (with cooling at 0° C.) to pH 1 with 2M $H_2SO_4$. The organic phase was extracted with 5% $NaHCO_3$ solution, and the bicarbonate solution was acidified to pH 1 and extracted with $CH_2Cl_2$ (3*50 ml). Drying and concentration afforded pale yellow oil which was crystallized at −20° C. from hexanes, affording colorless crystals of intermediate b (6.0 g, white solid, Yield=57%).

Intermediate b (5.0g, 23.5mmol) in EtOAc(115mL) was hydrogenated over Lindlar catalyst (117mg). The mixture was stirred at room temperature overnight. The mixture was filtered through Celite and washed with ethyl acetate (2*20ml). The solution was warmed to 35° C. for 10min, washed with 5% NaHCO3, dried and concentrated and chromatography gave compound 6. (1.25g, 27%, white solid at 0° C. and colorless oil at room temperature).

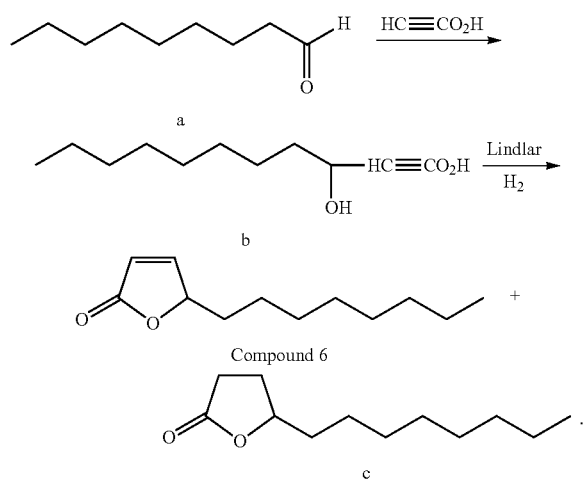

After the synthesis reactions, they were purified by HPLC. Then the molecular weight of compounds 5 and 6 was determined by negative ESI-MS (Waters Micromass ZQ ESI-MS). And its structure was detected by means of NMR ($^1$H NMR, $^{13}$C NMR) as following.

Compound 5: $^1$H NMR (400 MHz, $CDCl_3$) 7.44 (dd, J=6.0, 1.6 Hz, 1H), 6.09 (dd, J=6.0, 2.4 Hz, 1H), 5.05-5.00 (m, 1H), 4.60-4.56 (m, 1H), 3.95-3.82 (m, 1H), 3.68-3.55 (m, 1H), 3.52-3.42 (m, 1H), 1.90-1.20 (m, 17H), 1.11 (d, J=6.0 Hz, 3H), 0.82 (d, J=6.8 Hz, 3H); $^{13}$C NMR (100 MHz, $CDCl_3$) 173.1, 156.3, 121.5, 98.7, 83.4, 74.7, 62.9, 37.0, 33.1, 32.7, 31.2, 29.6, 27.2, 25.5, 24.9, 20.1, 16.9, 14.0

Compound 6: $^1$H NMR (500 MHz, $CDCl_3$) δ: 7.44 (1H, dd, J=5.7, 1.2 Hz, H-3), 6.09 (1H, dd, J=5.7, 1.9 Hz, H-2), 5.02 (1H, m, H-4), 1.74 (1H, m, H-5a), 1.65 (1H, m, H-5b), 0.86 (3H, t, J=6.8 Hz, Me-12); $^{13}$C NMR (125 MHz, $CDCl_3$) δ: 173.1 (C-1), 156.3 (C-3), 121.5 (C-2), 83.5 (C-4), 33.2 (C-5), 31.8 (C-10), 29.3 (C-7), 29.3 (C-8), 29.1 (C-9), 25.0 (C-6), 22.6 (C-11), 14.1 (C-12).

Based on above data, these two compounds were identified as:

Compound 5:

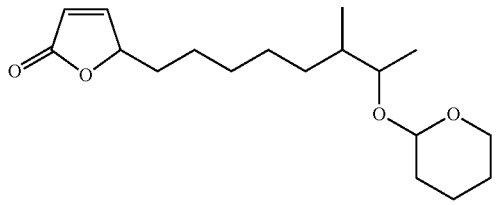

Compound 6:

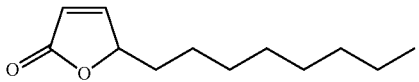

D. Bioassay for Antifouling Activity of Substituted Furan-2-One Compounds Against Larval Settlement Nauplii were obtained from the adult barnacles B. amphitrite collected from the intertidal zone in Hong Kong (22°19'N, 114°16'E). The nauplii were reared in freshly filtered nature seawater (FSW, 0.45 μm, 32 S salinity) and fed with Chaetoceros gracilis Schutt at 24° C. in the Coastal Marine Laboratory the Hong Kong University of Science and Technology (HKUST). Cyprids were stored for 2 days at 8° C. (aged cyprids) prior to being used in the bioassays. Ten μl of each test sample dissolved in dimethyl sulfoxide (DMSO) were transferred into a well in 24-well polystyrene plate after the addition of 1 ml of FSW. The control wells contained 1 ml of FSW and 10 μl of DMSO. About 15 cyprids were added in each well with triplicate samples being tested. The numbers of settled juveniles, dead or the moving larvae in each well were counted after 24 h of incubations at 24° C. in the dark to calculate $EC_{50}$ or $LC_{50}$.

Adults of Hydroides elegans (Haswell) were collected from a fish farm at Yung Shue O, Hong Kong (22°25'N, 114°16'E). Larvae were reared to the competent stage using the chrysophyte Isochrysis galbana (Tahitian strain) as food, aerated, and maintained at 25° C. on a 15 h light/9 h dark photoperiod according to Lau and Qian (1997). Competent larvae were incubated with $10^{-4}$M IBMX (a pharmacological compound that can effectively induce larval settlement of H. elegans (Bryan et al. 1997) for 0.5 h and rinsed with FSW being used for bioassays. Ten μl of sample solution of different concentrations were transferred into a well in 24-well polystyrene plate after the addition of 1 ml of FSW. About 10 competent larvae were added to each well with five replicates. Wells containing only 1 ml FSW served the positive (the added larvae were incubated for 0.5 h in the presence of IBMX) or negative controls (the added larvae were incubated for 0.5 h in the absence of IBMX) (Bryan et al. 1997). The 24-well plates were incubated at 28° C. for 24 h under a 15 h light/9 h dark photoperiod. The percentage of larval settlement and larval mortality was determined by counting the settled, live individuals under a dissecting microscope and expressing the result as a proportion of the total number of larvae in the well.

The results were shown in FIGS. 2-9 and the $EC_{50}$, $LC_{50}$, and $LC_{50}/EC_{50}$ values were calculated based on their inhibition effects and shown in Table 1. The results indicated that Compounds 1-3 can efficiently inhibited larval settlement of both B. amphitrite and H. elegans while compound 4 is efficient against the larval settlements especially for B. amphitrite. Through the comparison between the treated larval settlement and the controls, we observed the significant inhibition activity against larvae settlement of compound 1 was observed at a concentration of 10 μg/ml against B. amphitrite and H. elegans. For compound 2, it can significantly inhibit larvae settlement at a concentration of 10 μg/ml against B. amphitrite and at a concentration of 5 μg/ml against H. elegans. At the concentration of 25 and 5 μg/ml, the presence of compound 3 significantly reduced the settlement rate for B. amphitrite and H. elegans, respectively. Different with compound 1-3, compound 4 with a shorter side chain is less lipophilic, its efficient inhibition effect against larval settlement was only observed on H. elegans at a concentration of 8 μg/ml.

TABLE 1

EC$_{50}$, LC$_{50}$, and LC$_{50}$/EC$_{50}$ values of furanones against larval settlement of the barnacle *Balanus amphitrite*, *Bugula neritina*, and *Hydroides elegans* (μg ml$^{-1}$). For each compound, the EC$_{50}$ value presented here is mean of at least three replicates; the LC$_{50}$ value used for calculation of LC$_{50}$/EC$_{50}$ is the highest concentrations examined in the bioassay causing <50% death of larvae.

| Samples | *Balanus amphitrite* | | | *Hydroides elegans* | | | *Bugula neritina* | | |
|---|---|---|---|---|---|---|---|---|---|
| | EC$_{50}$ | LC$_{50}$ | LC$_{50}$/EC$_{50}$ | EC$_{50}$ | LC$_{50}$ | LC$_{50}$/EC$_{50}$ | EC$_{50}$ | LC$_{50}$ | LC$_{50}$/EC$_{50}$ |
| Compound 1 | 14.81 | >100 | >5.9 | 12.0 | >100 | >8.3 | Not Detected | | |
| Compound 2 | 9.65 | >100 | >8.8 | 4.4 | >100 | >22.7 | | | |
| Compound 3 | 8.67 | >100 | >8.5 | 5.6 | >100 | >17.9 | | | |
| Compound 4 | >100 | >140 | — | 12.7 | >40 | >16.7 | | | |
| Compound 5 | 3.6 | >80 | >27.8 | 6.4 | >100 | >15.6 | | | |
| Compound 6 | 0.52 | >50 | >97 | 0.017 | >2 | >119 | 0.2 | >50 | >250 |

Figure 10:
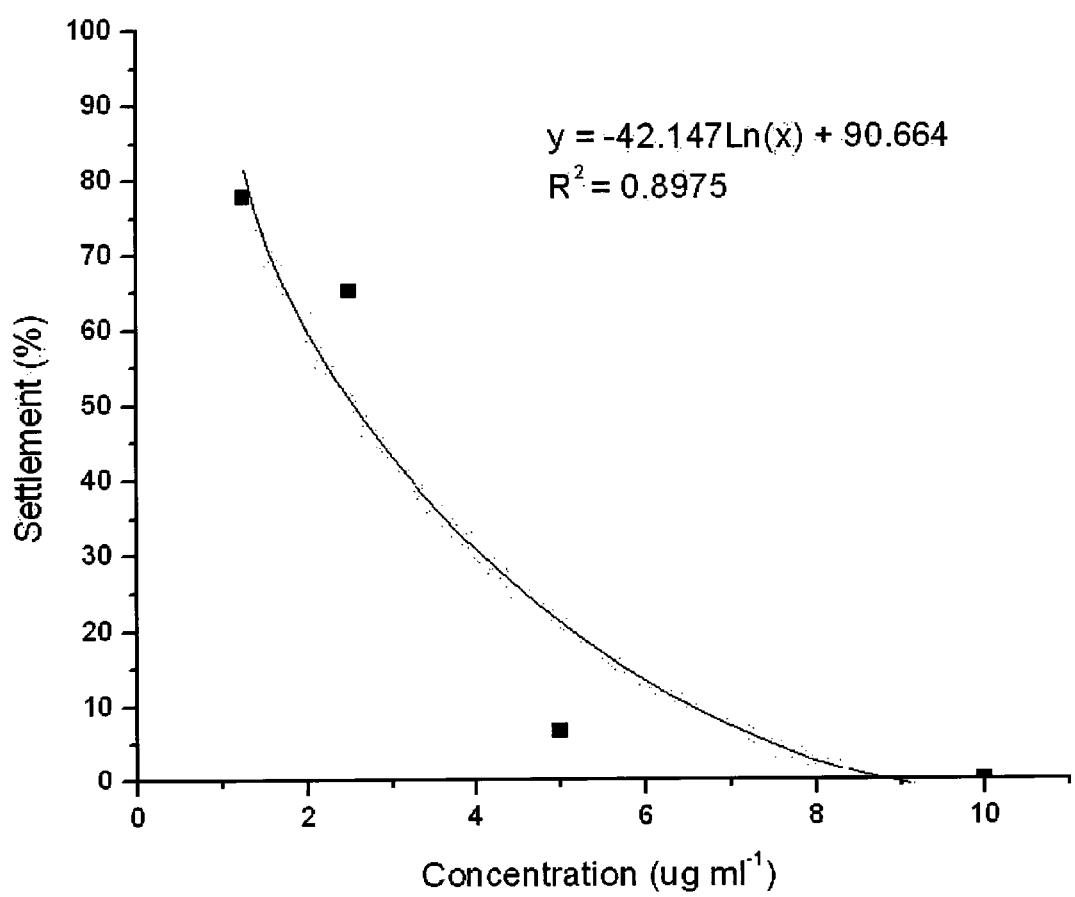
FIG. 10 shows the effect of Compound 5 against larval settlement of the barnacle *Balanus amphitrite*. The results were presented as the mean±standard deviation of at least three replicates (n>=3). The equation analysis was performed by Origin Pro. 7.5.
Figure 11:
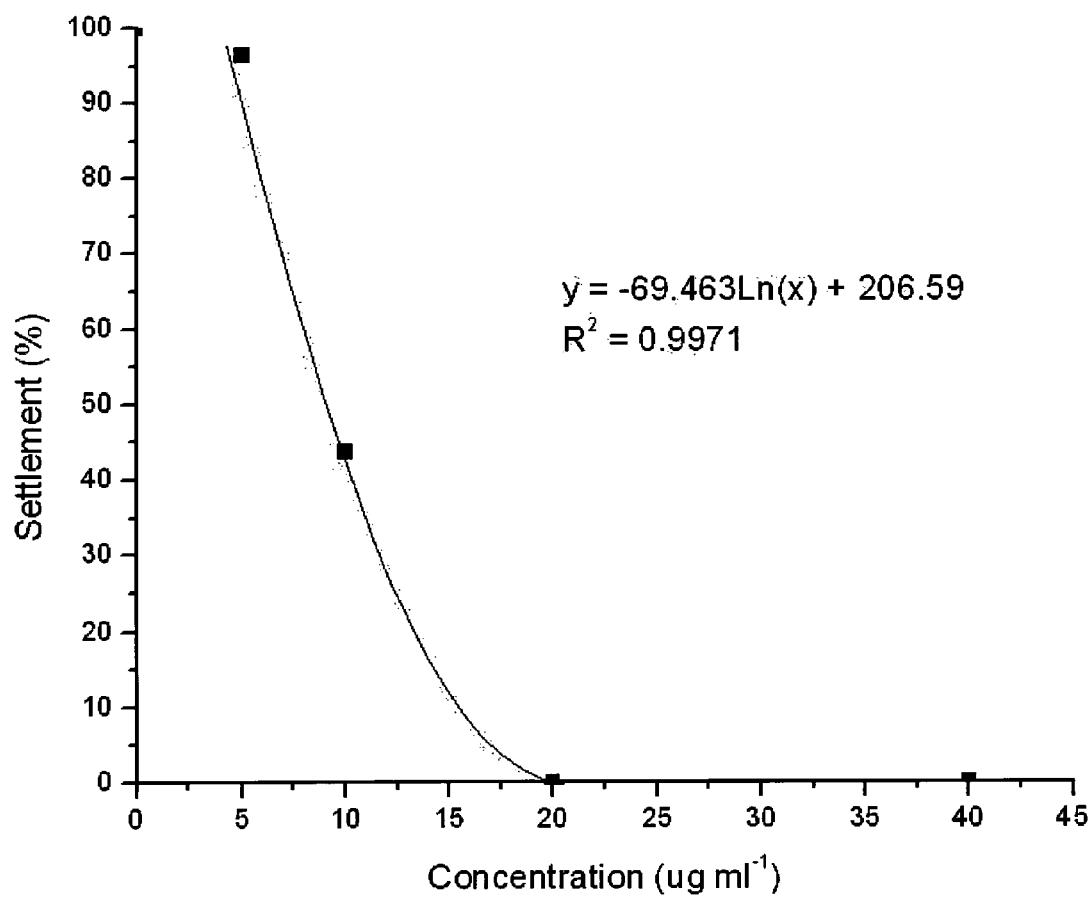
FIG. 11 shows the effect of Compound 5 against larval settlement of the barnacle *Bugula neritina*. The results were presented as the mean±standard deviation of at least three replicates (n>=3). The equation analysis was performed by Origin Pro. 7.5.
Figure 12:
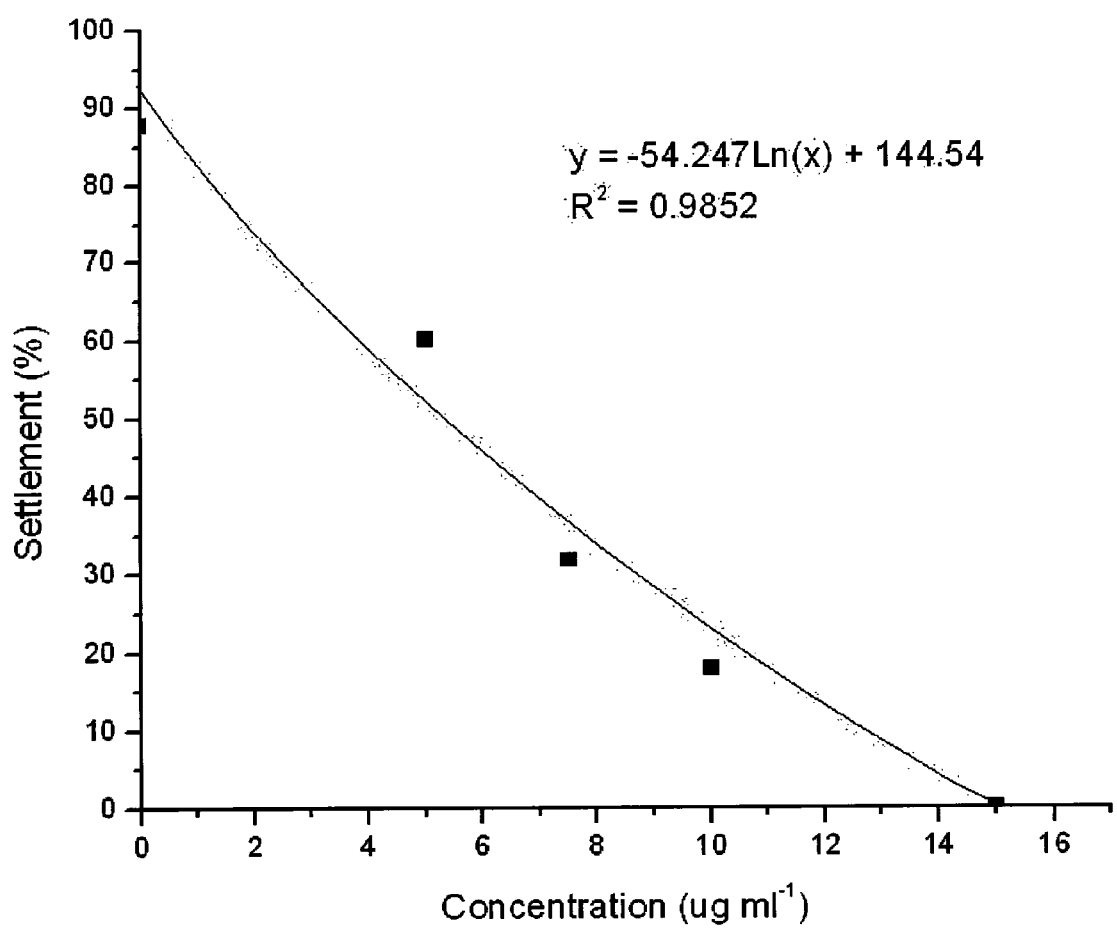
FIG. 12 shows the effect of Compound 5 against larval settlement of the barnacle *Hydroides elegans*. The results were presented as the mean±standard deviation of at least three replicates (n>=3). The equation analysis was performed by Origin Pro. 7.5.

For the synthetic compounds, i.e., compounds 5 and 6, potent antifouling effects were also observed. The results of compound 5 inhibiting the larval settlement against *B. amphitrite*, *B. neritina*, and *H. elegans* were shown in FIGS. 10, 11, and 12, respectively, and the EC$_{50}$, LC$_{50}$, and LC$_{50}$/EC$_{50}$ values were calculated based on the inhibition effects and shown in Table 1. The distinct inhibition effects against all three larval settlements were observed at quite low concentration. The LC$_{50}$/EC$_{50}$ value for this compound against *B. amphitrite*, *B. neritina*, and *H. elegans* were >27.8, >15.6 and >10.5 respectively, which indicated that it is a nontoxic or low toxic compound according to Avelin et al. 1993 and Rittschof et al. 1994.

Figure 13:
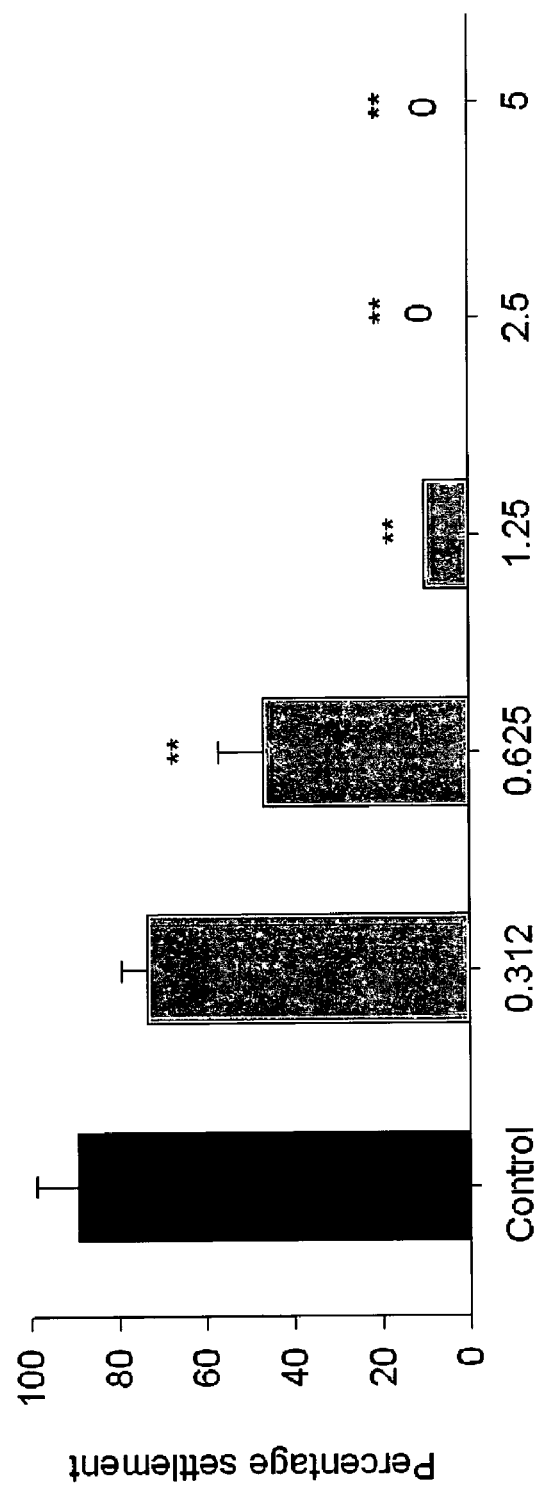
FIG. 13 shows the effect of Compound 6 against larval settlement of the barnacle *Balanus amphitrite*. The results were presented as the mean±standard deviation of at least three replicates (n>=3). The equation analysis was performed by Origin Pro. 7.5.
Figure 14:
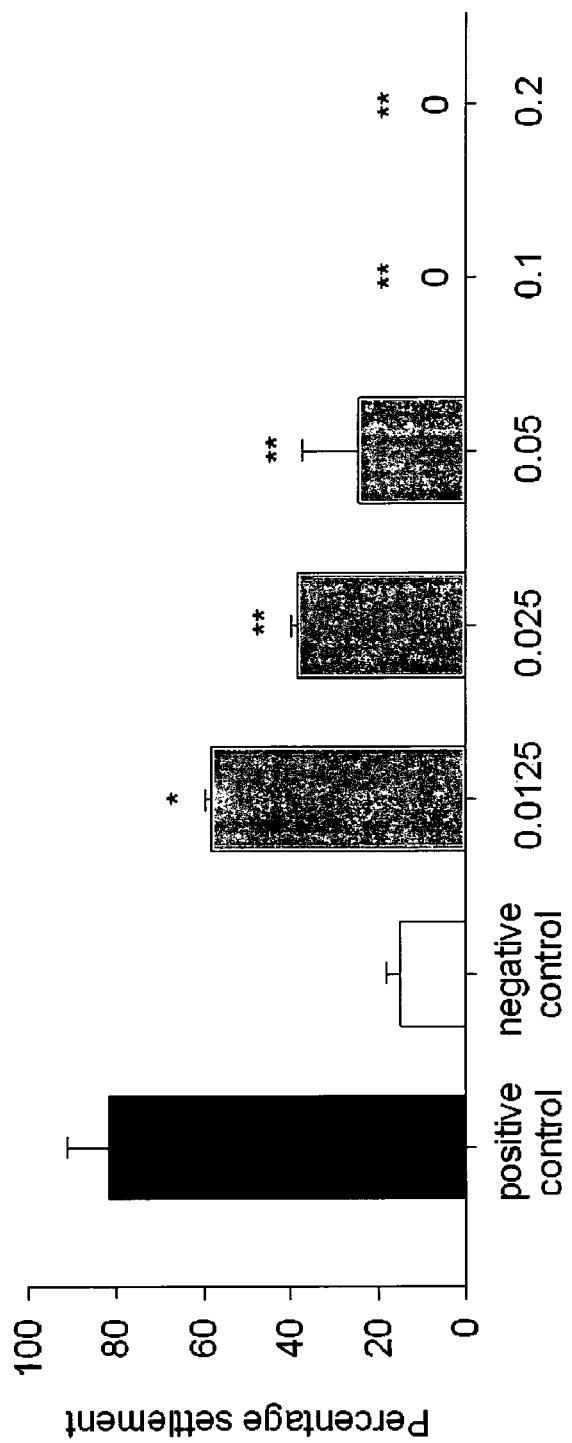
FIG. 14 shows the effect of Compound 6 against larval settlement of the barnacle *Hydroides elegans*. The results were presented as the mean±standard deviation of at least three replicates (n>=3). The equation analysis was performed by Origin Pro. 7.5.
Figure 15:
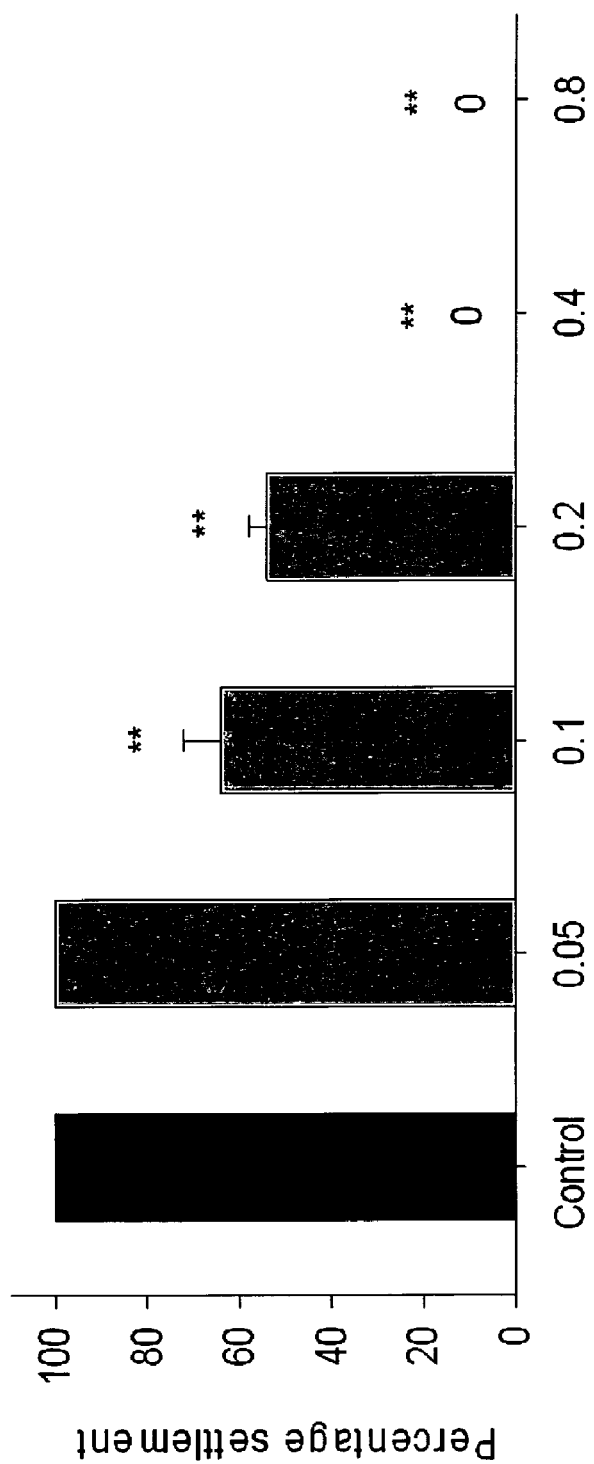
FIG. 15 shows the effect of Compound 6 against larval settlement of the barnacle *Bugula neritina*. The results were presented as the mean±standard deviation of at least three replicates (n>=3). The equation analysis was performed by Origin Pro. 7.5.
Figure 16:
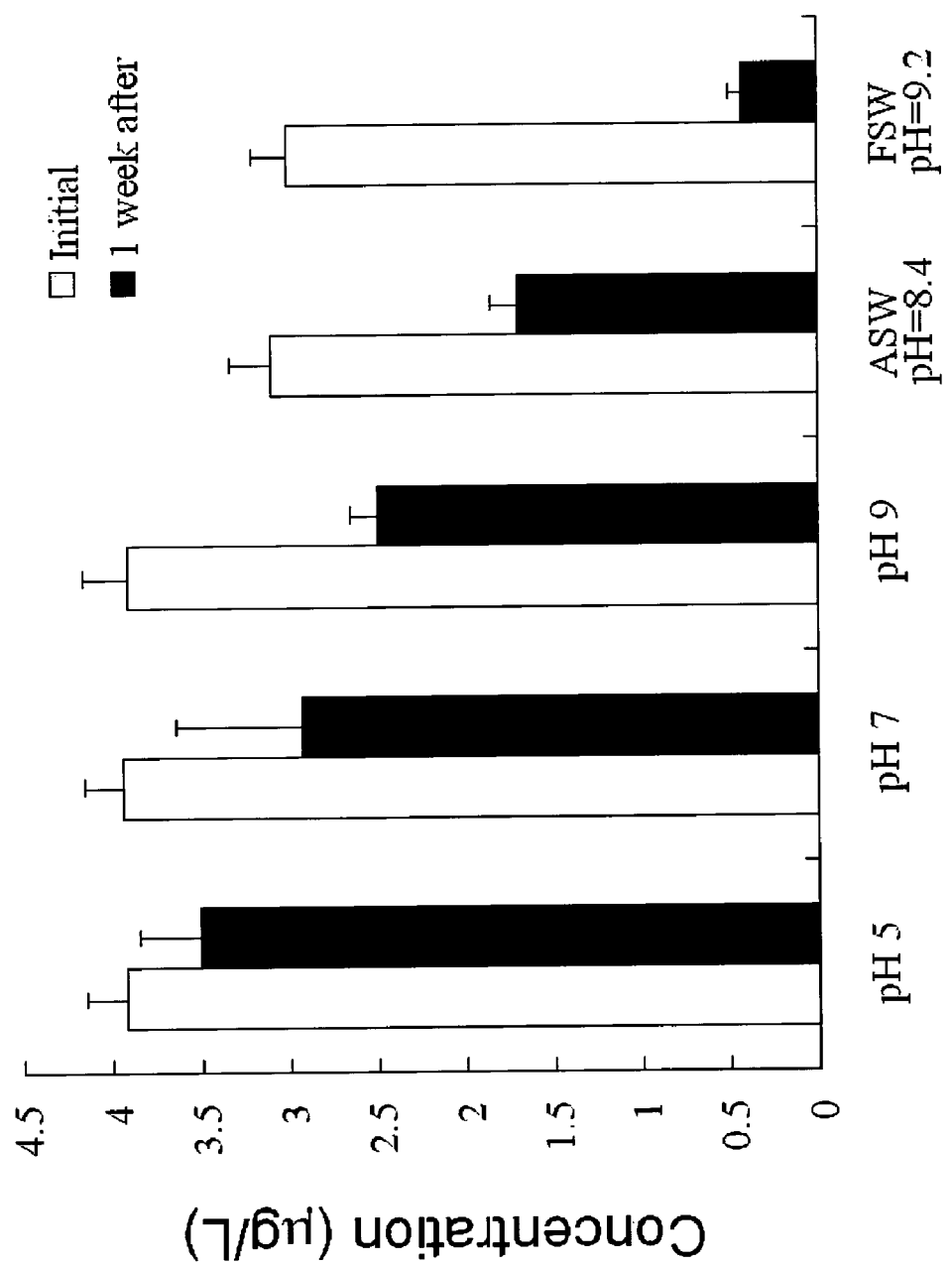
FIG. 16 shows degradation of Compound 6 in buffer solutions of different pH values as well as in seawater with adjusted pH values (n=5): ASW—artificial seawater; FSW—0.25 mm filtered seawater.

The results of compound 6 inhibiting the larval settlement against *B. amphitrite*, *B. neritina*, and *H. elegans* were shown in FIGS. 13, 14, and 15, respectively, and the EC$_{50}$, LC$_{50}$, and LC$_{50}$/EC$_{50}$ values were calculated based on the inhibition effects and shown in Table 1. The distinct inhibition effects against all three larval settlements were observed at quite low concentration. The LC$_{50}$/EC$_{50}$ value for this compound against *B. amphitrite*, *B. neritina*, and *H. elegans* were >97, >119 and >250, which indicated it is a nontoxic or low toxic compound according to Avelin et al. 1993 and Rittschof et al. 1994.

Figure 6:
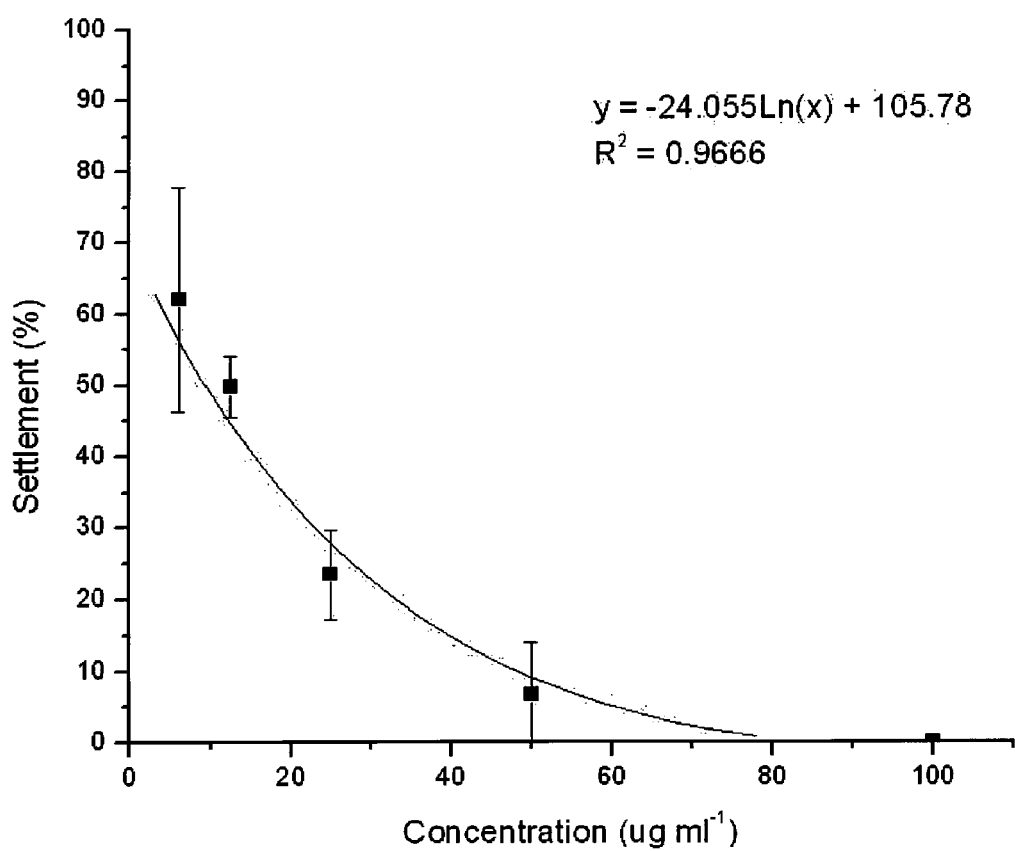
FIG. 6 shows the effect of Compound 3 against larval settlement of the barnacle *Balanus amphitrite*. The results were presented as the mean±standard deviation of at least three replicates (n>=3). The equation analysis was performed by Origin Pro. 7.5.
Figure 7:
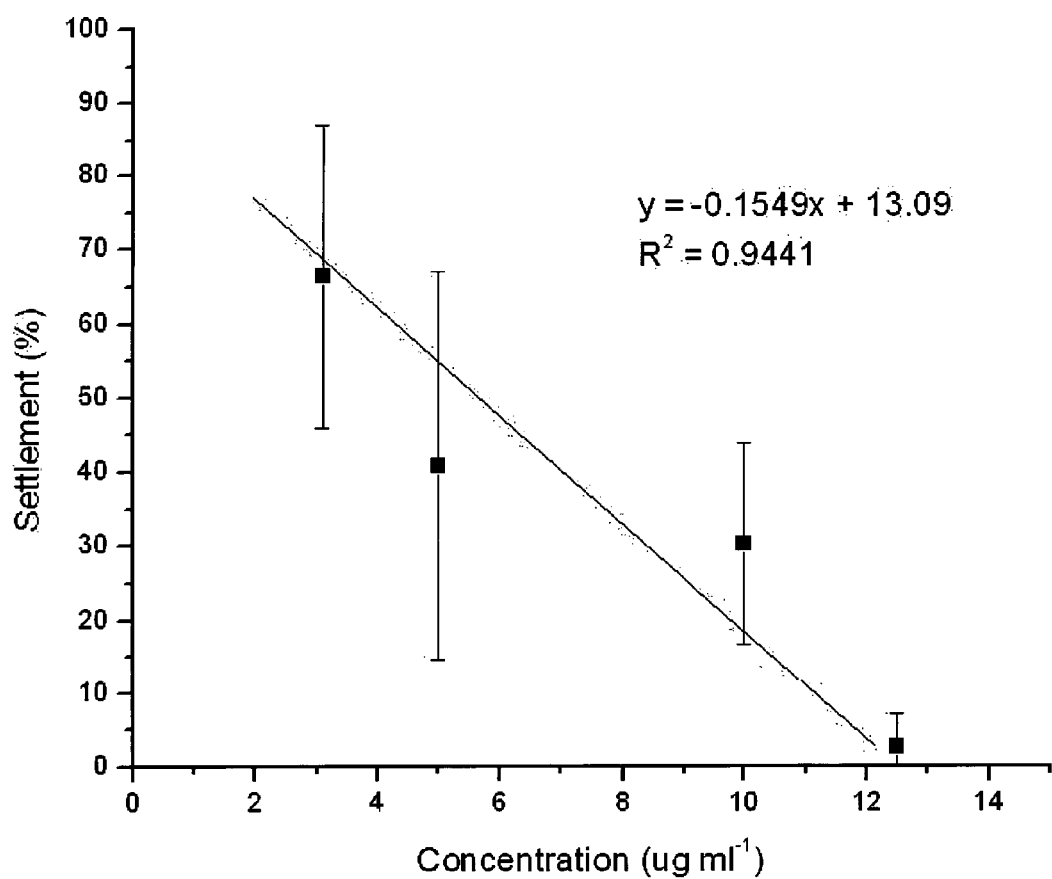
FIG. 7 shows the effect of Compound 3 against larval settlement of the barnacle *Hydroides elegans*. The results were presented as the mean±standard deviation of at least three replicates (n=3). The equation analysis was performed by Origin Pro. 7.5.
Figure 8:
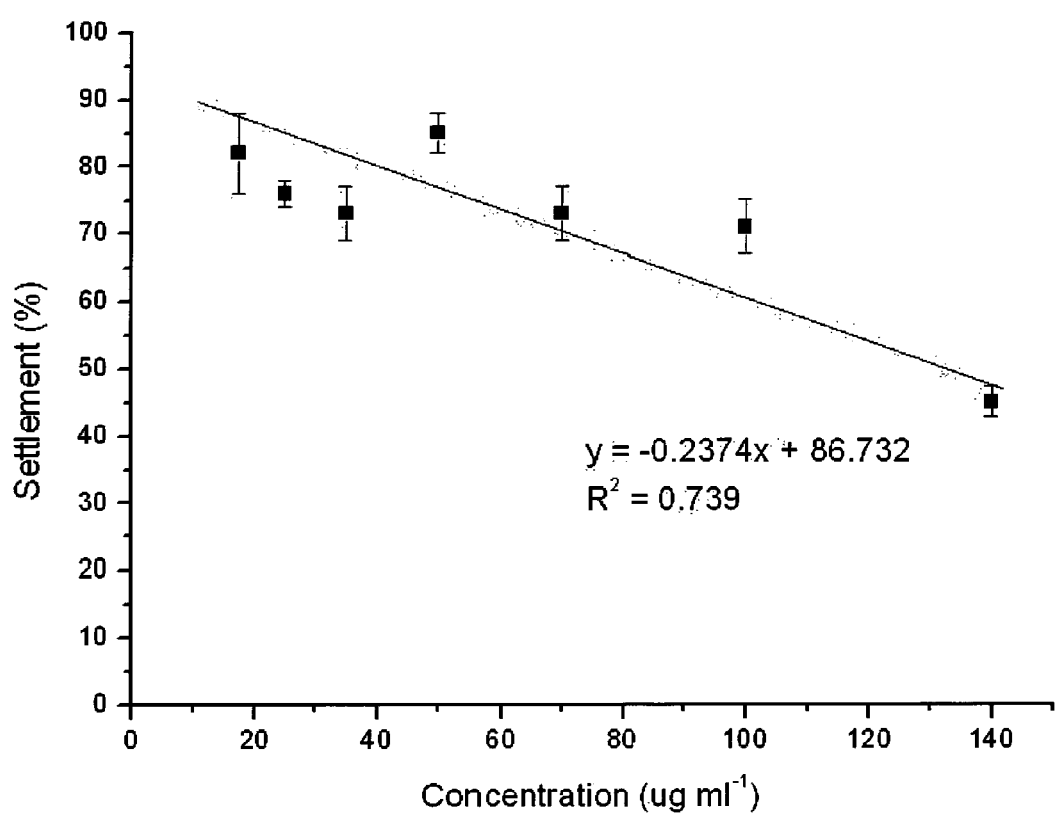
FIG. 8 shows the effect of Compound 4 against larval settlement of the barnacle *Balanus amphitrite*. The results were presented as the mean±standard deviation of at least three replicates (n=3). The equation analysis was performed by Origin Pro. 7.5.
Figure 9:
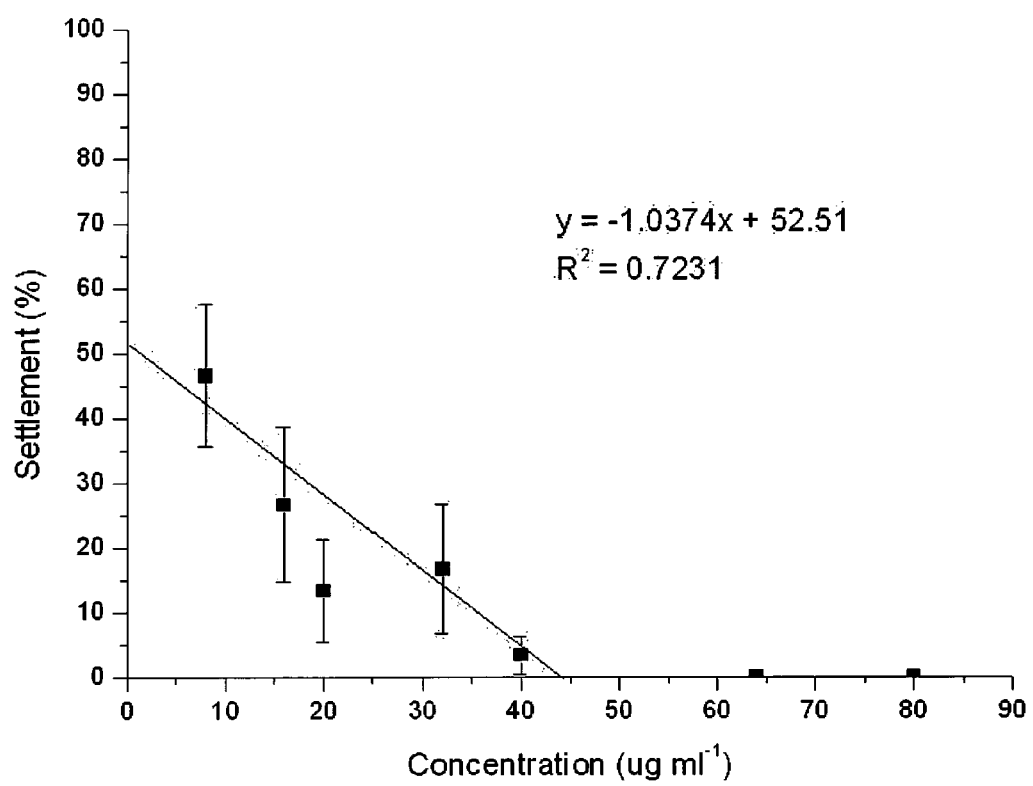
FIG. 9 shows the effect of Compound 4 against larval settlement of the barnacle *Hydroides elegans*. The results were presented as the mean±standard deviation of at least three replicates (n>=3). The equation analysis was performed by Origin Pro. 7.5.

In addition, the above compounds did not show any toxicity against tested larvae at the concentrations involved in the bioassays in present invention. And the ratio of LC$_{50}$/EC$_{50}$ in Table 1 also indicates they are nontoxic or low toxic compounds according to Avelin et al. 1993 and Rittschof et al. 1994. Furthermore, FIG. 6 shows that compound 6 can be easily degradated in natural seawater.

The above specific substituted furan-2-one antifouling compounds can be utilized as a guideline for design of environment-friendly antifoulants by chemical modification to achieve high activities or to reduce cost. The chemical modification of the compounds in present invention may be carried out with conventional methods known to people having ordinary skill in the art based on a rational design in view of the activity-structure relationship disclosed in the prevent invention. The following compounds were included in the activity-structure relationship study intended to provide a guideline to practice the present invention beyond the specific embodiments provided in the foregoing. For example, as shown in Table 3, the results of experiments have demonstrated that nontoxic and potent antifouling compounds of the present invention should have the following furan motif and any modifications on this motif would likely to render the compound unsuitable as an antifouling agent (for example, compounds 8, 9, and 10).

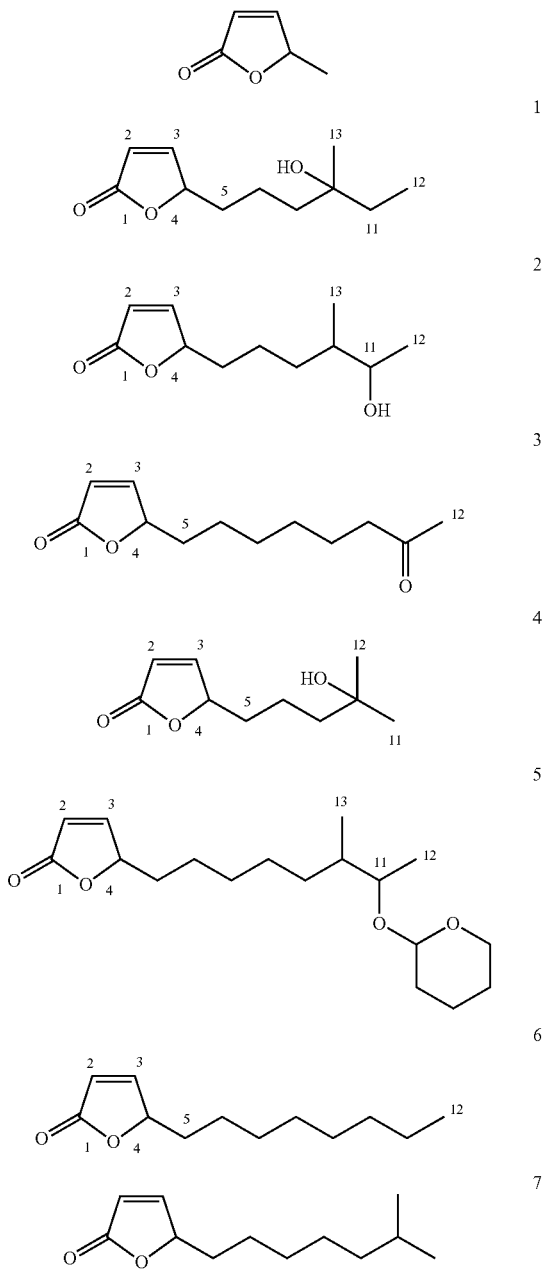

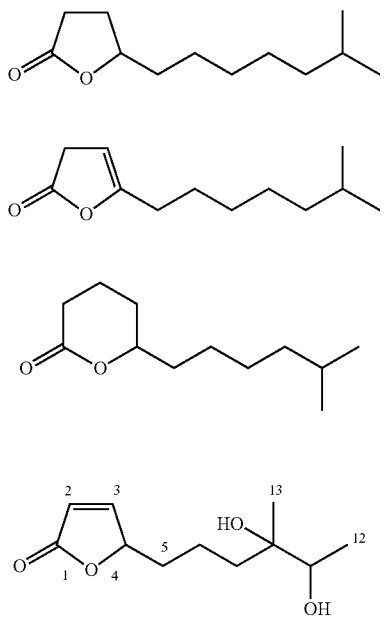

TABLE 3

| | Balanus amphitrite larvae | | |
| Compound | EC$_{50}$ (µg ml$^{-1}$) | LC$_{50}$ (µg ml$^{-1}$) | LC/EC$_{50}$ |
|---|---|---|---|
| 1 | 14.81 ± 5.54 | >100 | >6 |
| 2 | 9.65 ± 1.50 | >100 | >10 |
| 3 | 8.67 ± 2.73 | >100 | >11 |
| 4 | >100 | >140 | — |
| 5 | 3.6 ± 0.56 | >80 | >27 |
| 6 | 0.52 ± 0.06 | >50 | >97 |
| 7 | 4.82 ± 1.25 | >25 | >5 |
| 8 | >100 | >100 | — |
| 9 | >100 | >100 | — |
| 10 | >100 | >100 | — |
| 11 | >100 | >100 | — |

— not applicable

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

---

What is claimed is:

1. A method of preventing or reducing biofouling on a surface of an object submerged in water, comprising a step of applying a coating material to said surface of said object, wherein said coating material comprising at least one substituted furan-2-one antifouling compounds of formula I, having a 5-membered ring and a side chain:

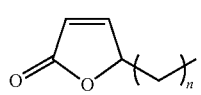

I where n=6-14, representing the number of carbons in said side chain.

2. The method of claim 1, wherein said side chain is substituted.

3. The method of claim 1, wherein n is 7-10 and said side chain is non-substituted.

4. The method of claim 1, wherein n is 7-10 and said side chain is non-branched.

5. The method of claim 1, wherein said side chain is substituted by a OH group or =O group.

6. The method of claim 4, wherein said side chain is non substituted.

7. The method of claim 1, wherein said side chain has a first segment being attached to said 5-membered ring, said first segment having at least 5 carbon atoms and being straight without a branch or a substituent.

8. A coating material for preventing biofouling, comprising (a) at least one substituted furan-2-one antifouling compound, and (b) a carrier suitable for making a coating material, wherein said substituted furan-2-one antifouling compound is of formula I, having a 5-membered ring and a side chain:

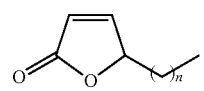

I where n=6-14, representing the number of carbon atoms in said side chain.

9. The coating material of claim 8, wherein n is 7-10 and said side chain is non-substituted.

10. The coating material of claim 9, wherein said side chain is non-branched.

11. The coating material of claim 8, wherein said side chain is substituted by a OH group or =O group.

12. The coating material of claim 8, wherein said side chain has a first segment being attached to said 5-membered ring, said first segment having at least 5 carbon atoms and being straight without a branch or a substituent.

13. The coating material of claim 8, wherein said substituted furan-2-one antifouling compound is selected from the group consisting of

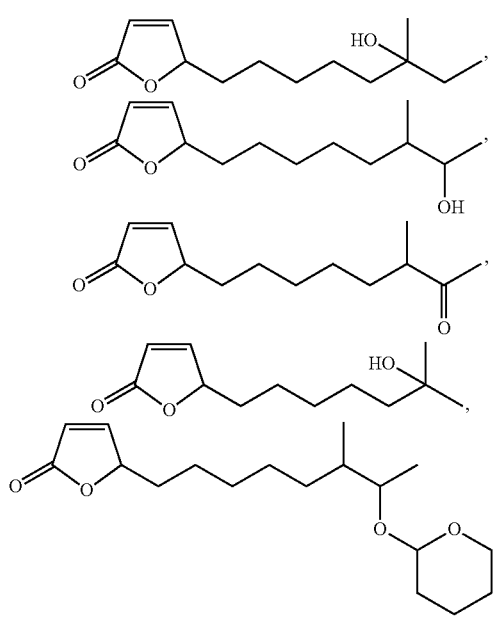
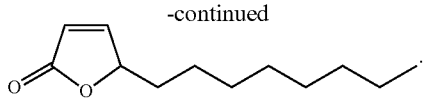
14. The substituted furan-2-one antifouling compound, which is which is selected from the group consisting of
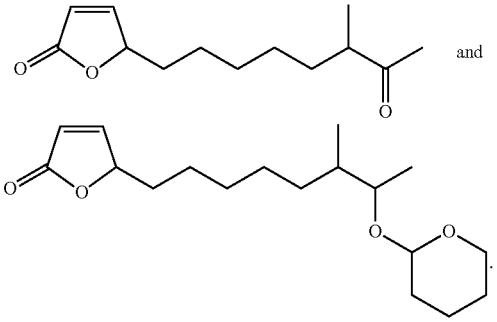
* * * * *

UNITED STATES PATENT AND TRADEMARK OFFICE
CERTIFICATE OF CORRECTION

| | |
|---|---|
| PATENT NO. | : 8,177,896 B2 |
| APPLICATION NO. | : 13/054938 |
| DATED | : May 15, 2012 |
| INVENTOR(S) | : Qian et al. |

It is certified that error appears in the above-identified patent and that said Letters Patent is hereby corrected as shown below:

On the Title page, (56) References Cited, OTHER PUBLICATIONS, the last reference "De-Hai Li et al, "Four butenolides are novel cytotoxic compounds isolated from the marine-derived bacterium, *Streptoverticillium luteoverticillatum* 11014", Arch Pharm Res. vol. 29, No. 8, pp. 624-626, 2006." should be deleted because it is a duplicate of the first reference.

On the cover page, (57) ABSTRACT, the chemical compound

" 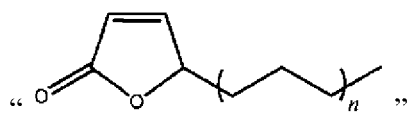 "

Should read:

-- 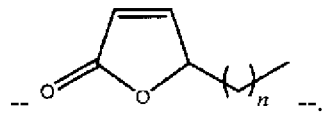 --.

In Column 2, line 44, "n is 8" should read --n is 7--.

In Column 6, line 38, "Si02 and CH2C12" should read --$SiO_2$ and $CH_2Cl_2$--.

In Column 6, line 39, "30oC" should read --30°C--.

Signed and Sealed this
Twentieth Day of November, 2012

David J. Kappos
*Director of the United States Patent and Trademark Office*

In Column 6, lines 42-50, Compound 2 should be changed from
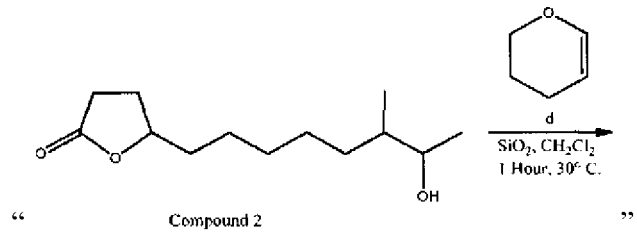
" Compound 2 "
to
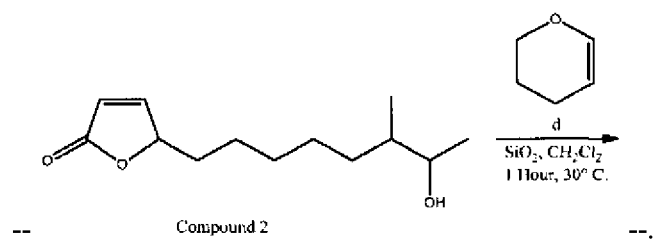
-- Compound 2 --.
In Column 6, lines 51-58, Compound 5 should be changed from:
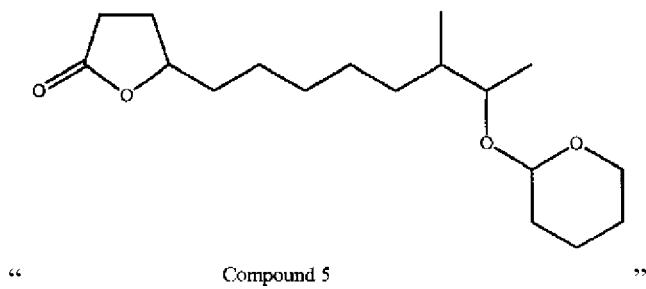
" Compound 5 "
to
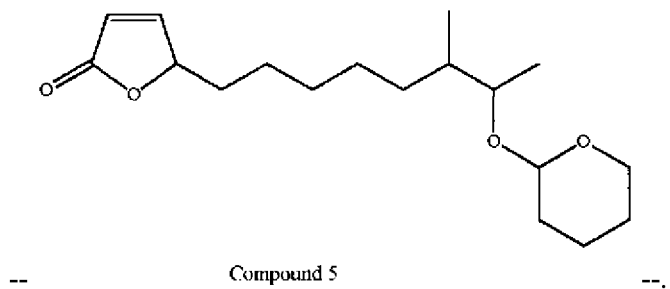
-- Compound 5 --.
In Column 12, line 5, the fourth heading of the table, "LC/EC$_{50}$", should be changed to read --LC$_{50}$/EC$_{50}$--.
In Column 16, line 8, the first two words, "which is", should be deleted because they are duplicative.

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
agagtttgat cmtggctcag          20

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
ggttaccttg ttacgactt          19

<210> SEQ ID NO 3
<211> LENGTH: 1413
<212> TYPE: DNA
<213> ORGANISM: Streptomyces albidoflavus

<400> SEQUENCE: 3
tgcttaacac atgcaagtcg aacgatgaac cgctttcggg cggggattag tggcgaacgg     60
gtgagtaaca cgtgggcaat ctgccctgca ctctgggaca gcccctggaa acggggtcta    120
ataccggata tgacygtcyg ccgcatggtg gatggtgtaa agctccggcg gtgcaggatg    180
agcccgcggc ctatcagctt gttggtgagg tagtggctca ccaaggcgac gacgggtagc    240
cggcctgaga gggcgaccgg ccacactggg actgagacac ggcccagact cctacgggag    300

```
gcagcagtgg ggaatattgc acaatgggcg aaagcctgat gcagcgacgc cgcgtgaggg      360
atgacggcct tcgggttgta aacctctttc agcagggaag aagcgaaagt gacggtacct      420
gcagaagaag cgccggctaa ctacgtgcca gcagccgcgg taatacgtag ggcgcaagcg      480
ttgtccggaa ttattgggcg taaagagctc gtaggcggct tgtcacgtcg gttgtgaaag      540
cccgggcgtt aaccccgggt ctgcagtcga tacgggcagg ctagagttcg gtaggggaga      600
tcggaattcc tggtgtagcg gtgaaatgcg cagatatcag gaggaacacc ggtggcgaag      660
gcggatctct gggccgatac tgacgctgag gagcgaaagc gtggggagcg aacaggatta      720
gataccctgg tagtccacgc cgtaaacggt gggcactagg tgtgggcaac attccacgtt      780
gtccgtgccg cagctaacgc attaagtgcc ccgcctgggg agtacggccg caaggctaaa      840
actcaaagga attgacgggg gcccgcacaa gcggcggagc atgtggctta attcgacgca      900
acgcgaagaa ccttaccaag gcttgacata caccggaaac gtctggagac aggcgccccc      960
ttgtggtcgg tgtacaggtg gtgcatggct gtcgtcagct cgtgtcgtga gatgttgggt     1020
taagtcccgc aacgagcgca accttgtcc cgtgttgcca gcaggcccctt gtggtgctgg     1080
ggactcacgg gagaccgccg gggtcaactc ggaggaaggt ggggacgacg tcaagtcatc     1140
atgccccta tgtcttgggc tgcacacgtg ctacaatggc cggtacaatg agctgcgata     1200
ccgcgaggtg gagcgaatct caaaaagccg gtctcagttc ggattggggt ctgcaactcg     1260
accccatgaa gtcggagtcg ctagtaatcg cagatcagca ttgctgcggt gaatacgttc     1320
ccgggccttg tacaccgcc ccgtcacgtc acgaaagtcg gtaacacccg aagccggtgg     1380
cccaaccct tgtgggaggg agctgtcgaa ggt                                   1413
```